United States Patent [19]

Blair et al.

[11] Patent Number: 5,187,980
[45] Date of Patent: Feb. 23, 1993

[54] METHOD AND APPARATUS FOR ACOUSTIC PLATE MODE LIQUID-SOLID PHASE TRANSITION DETECTION

[75] Inventors: Dianna S. Blair, Albuquerque; Gregory C. Frye, Cedar Crest; Robert C. Hughes, Albuquerque; Stephen J. Martin, Albuquerque; Antonio J. Ricco, Albuquerque, all of N. Mex.

[73] Assignee: The United States of America as represented by the United States Department of Energy, Washington, D.C.

[21] Appl. No.: 531,492

[22] Filed: May 31, 1990

[51] Int. Cl.$^5$ .................. G01N 9/24; G08B 19/02
[52] U.S. Cl. .................................. 73/599
[58] Field of Search .................. 73/599, 597, 596; 340/582, 580, 962; 310/311, 313 R

[56] References Cited

U.S. PATENT DOCUMENTS

| | | | |
|---|---|---|---|
| 3,341,835 | 9/1967 | Werner et al. | 340/234 |
| 3,706,981 | 12/1972 | Hart | 340/244 R |
| 4,054,255 | 10/1977 | Magenheim | 244/134 F |
| 4,335,613 | 6/1982 | Luukkala | 73/599 |
| 4,378,168 | 3/1983 | Kuisma et al. | 73/599 |
| 4,404,852 | 9/1983 | Goto | 73/599 |
| 4,461,178 | 7/1984 | Chamuel | 73/599 |
| 4,532,806 | 8/1985 | Bruchmuller | 73/579 |
| 4,568,922 | 2/1986 | Schwippert et al. | 340/582 |
| 4,604,612 | 8/1986 | Watkins et al. | 340/582 |
| 4,611,492 | 9/1986 | Koosmann | 73/579 |
| 4,628,736 | 12/1986 | Kirby et al. | 73/590 |

OTHER PUBLICATIONS

A. Ricco et al., "Acoustic Wave Viscosity Sensor", *Applied Physics Letters*, vol. 50, No. 21, May 25, 1987, pp. 1474–1476.

T. Nimeczyk et al., "Acoustoelectric Interaction of Plate Modes With Solutions", *Journal of Applied Physics*, vol. 64, No. 10, Part 1, Nov. 15, 1988, pp. 5002–5008.

S. Martin et al., "Sensing In Liquids With SH Plate Mode Devices" *Proceedings of the 1988 IEEE Ultrasonics Symposium*, vol. I, 1988, pp. 607–611.

*Primary Examiner*—Louis Arana
*Attorney, Agent, or Firm*—Anne D. Daniel; James H. Chafin; William R. Moser

[57] ABSTRACT

A method and apparatus for sensing a liquid-solid phase transition event is provided which comprises an acoustic plate mode detecting element placed in contact with a liquid or solid material which generates a high-frequency acoustic wave that is attenuated to an extent based on the physical state of the material is contact with the detecting element. The attenuation caused by the material in contact with the acoustic plate mode detecting element is used to determine the physical state of the material being detected. The method and device are particularly suited for detecting conditions such as the icing and deicing of wings of an aircraft. In another aspect of the present invention, a method is provided wherein the adhesion of a solid material to the detecting element can be measured using the apparatus of the invention.

2 Claims, 3 Drawing Sheets

METHOD AND APPARATUS FOR ACOUSTIC PLATE MODE LIQUID-SOLID PHASE TRANSITION DETECTION

The U.S. Government has rights in this invention pursuant to contract number DE-AC04-76DP00789 between the U.S. Department of Energy and AT&T Technologies, Inc.

FIELD OF THE INVENTION

The invention relates in general to a method and apparatus for carrying out acoustic plate mode liquid-solid phase transition detection, and more particularly to a device and method for detecting the freezing and melting of water or other liquids on a surface such as an airplane wing.

BACKGROUND OF THE INVENTION

Under a variety of weather conditions such as rain, sleet, hail or snow, the wings of an aircraft may be subject to the formation of ice on the wing surface which can be a severe hazard to navigation. Such an ice layer, if undetected, can cause an aircraft to go off course, or worse, result in an airplane crash particularly during take-offs or landings. The accurate detection of the formation of a layer of ice on airplane wings is thus a crucial element in safe air travel.

Various devices are known that have been used to monitor the development of a layer of ice on aircraft wings. For example, U.S. Pat. No. 4,604,612 (Watkins et al.) discloses a method of detecting ice formation utilizing two ultrasonic transducers spaced apart from each other wherein the second transducer is adapted to detect propagation of an ultrasonic wave from the first. This device operates at relatively low frequencies in the range of 250 Khz to 1 Mhz. The sensitivity of this device, which is inversely dependent on frequency, will thus not be as acute as in those devices having a much higher frequency. Another known device, as disclosed in U.S. Pat. No. 4,461,178 (Chamuel), also detects wing icing by monitoring variations in flexural waves transmitted through the outer plate material of an aircraft airfoil.

Recently, it has been found that acoustic wave devices utilizing a shear horizontal acoustic plate mode can yield a wealth of information regarding liquid-solid interfaces. Information regarding the viscosity of the liquid, the mass of solid films bound to the crystal surface under the liquid, the density of chemical species bound to the crystal surface, and the electrical properties of the liquid to be detected can all be obtained using those devices. It would be desirable, therefore, to develop a method and device for utilizing a shear horizontal acoustic plate mode which can be used to study the physical chemistry of liquid-solid phase transitions in general, and to provide a means by which icing conditions such as those that would occur on the wings of an aircraft could be monitored.

SUMMARY OF THE INVENTION

In accordance with the present invention, a sensing device for detecting liquid-solid phase transition events is provided which comprises:

a) an acoustic plate mode detecting element capable of generating a high frequency mechanical wave attenuated to a degree dependent on the physical state of a material to be detected on said element, and capable of transmitting a signal inversely proportional to said attenuation of said high frequency mechanical wave; and b) a signal receiving means capable of receiving the signal transmitted by said acoustic plate mode detecting element proportional to the attenuation of said high frequency mechanical wave which can be used to determine the physical state of the material being detected.

A method for employing the device of the present invention in applications such as sensing the development of ice on a metal surface, or the detection of bonding of particular materials to a particular surface is also provided.

DETAILED DESCRIPTION OF THE PREFERRED EMBODIMENTS

It has previously been demonstrated that acoustic wave devices utilizing shear horizontal (SH) acoustic plate modes (APMs) have been utilized in a number of tests relating to the sensing of the interactions between plates modes and solutions (see, e.g., Niemozyk et al., *J. App. Phys.* 64:5002 (1988), or Ricco et al., *Appl. Phys. Lett.* 50:1474 (1987)). Monitoring the perturbations of the propagation characteristics of acoustic plate mode devices has allowed for the measurement of liquid viscosity, mass density of interfacial films, density of chemical species found at the interface, and the electrical properties of solutions. However, acoustic plate mode (APM) devices have not been used in a method to determine the phase transition from a liquid to a solid so as to be useful in monitoring such situations as airplane wing icing.

Figure 1:
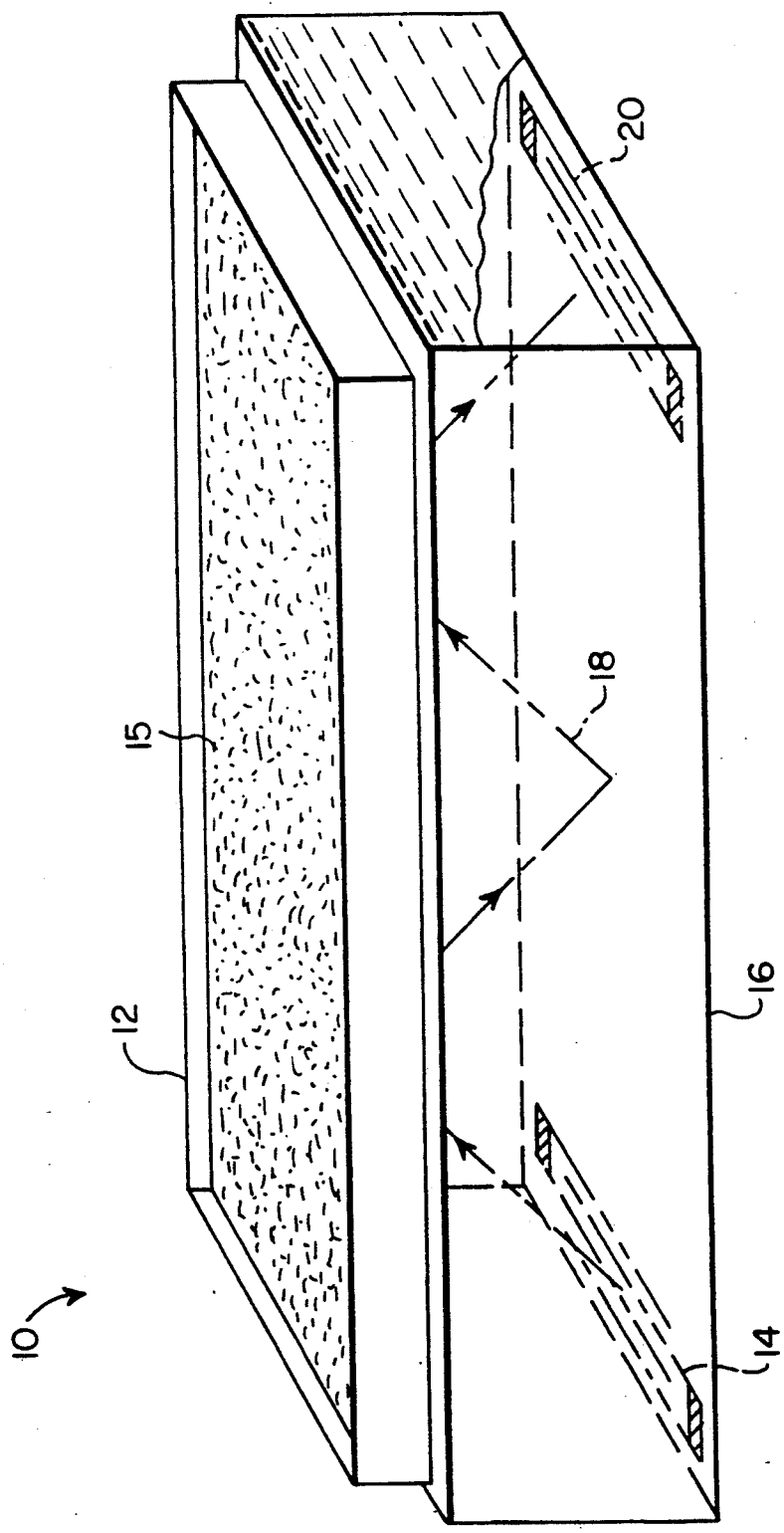
FIG. 1 is a schematic representation of the device of the present invention.

As observed in FIG. 1, the acoustic plate mode detecting element 10 of the present invention is positioned so that it will be contacted by a liquid 15 or other material whose physical state is to be detected. In most embodiments, such as when used on an airplane wing, the detecting element 10 will be placed flush on the wing, and material such as water or ice falling on or forming on the wing is directly detected. It is also possible, however, to employ a cell 12, as observed in FIG. 1, in order to retain the liquid or solid material to be detected. The cell 12 is made of Teflon or other suitable material which can retain the liquid or solid material to be detected, and which maintains contact with the surface of the device 10.

In this apparatus, SH-APMs are excited and detected by interdigital transducers patterned on one face of a piezoelectric quartz plate. In FIG. 1, it can be observed that the input transducer 14 generates a shear wave which is reflected off the upper and lower faces of the piezoelectric quartz plate 16. In the preferred embodiment, application of alternating electrical potential to the input transducers imposes an alternating strain field in the piezoelectric plate which launches a mechanical wave into the bulk of the quartz plate. The multiple reflection of this wave by the upper and lower faces leads to wave confinement so that the plate forms an acoustic waveguide. The superposition of reflective waves results in an SH plate mode characterized by sinusoidal variation of shear displacement across the plate with maxima at the upper and lower surfaces. When the APM wave 18 reaches the second or output transducer 20, it generates an electrical signal which transmits information about the attenuation and phase delay experienced by the acoustic mode as it traversed the plate. Because both surfaces of the APM device substrate undergo equal displacement as the wave propagates, either face can be used to probe a contacting medium. It is the signal transmitted by the output transducer inversely proportional to the attenuation of the mechanical wave, that will be used to determine the physical state of the material being detected.

A shear horizontal plate mode has displacement parallel to the surface of the device and perpendicular to the direction of mode propagation. When the liquid 15 contacts the quartz plate, this shear displacement entrains a thin layer of liquid which causes viscous damping of the APM. When the medium contacting the device surface undergoes a phase change from liquid to solid, its behavior changes from viscous to elastic. Consequently, the APM no longer entrains a thin layer adjacent to the plate, but instead radiates a shear wave into the bulk of the contacting solid. The radiated power "leaks away" from the propagating APM, and this causes substantial attenuation of the wave. The loss to the solid phase is related to how well the acoustic impedance of the adjacent solid matches that of the quartz plate. Because SH plate modes suffer minor attenuation when a liquid contacts the device surface, but undergo substantial attenuation with a solid in contact, they are very well suited for detecting liquid-to-solid phase changes. In the method of the invention, the high frequency mechanical wave which is attenuated to a degree dependent on the physical state of the material being detected in contact with the detecting element, either directly or as retained in cell 12, is used to determined the physical state of the material under detection.

In the preferred embodiment, the interdigital transducers of a device in accordance with the invention are defined photolithographically on an ST-cut quartz plate from roughly 200 nm thick Au-on-Cr metallization. The transducers are preferably composed of about 50 finger pairs each, having a periodicity of about 32 $\mu$m. This periodicity, together with an APM propagation velocity of approximately 5100 m/sec, results in the SH-APM excitation being most efficient at about 158 MHz. The unmetallized side of the device of the invention was lapped to obtain a thickness of roughly 165 $\mu$m and was polished to an optical finish. The device was mounted in a suitably sized flatpack, such as a 25.5 mm ×12.7 mm gold-plated steel flatpack with a 20.5 mm ×3.7 mm opening to allow liquid to contact the unelectroded side of the device. The unelectroded face of the device was bonded in the region surrounding the acoustic path to the opening in the flatpack using a bead of elastomer, preferably room temperature vulcanizing silicone rubber. Electrical contact was made between transducer bonding pads and flatpack feedthroughs by 25 $\mu$m diameter gold leads attached with an ultrasonic bonder. The flatpack was mounted in a brass test fixture containing impedance matching networks.

As can further be observed in FIG. 1, the liquid 15 was held in contact with the sensing surface when located in teflon cell 12, sealed by compression to the metal flatpack. About one milliliter of liquid was placed in the cell when testing of the device was desired. A miniature platinum resistance temperature device (RTD, $R_o$=100 Ohms) was freely suspended in the liquid to measure temperature. Controlled slow temperature ramps were obtained by placing the entire assembly in a variable temperature environmental chamber.

In carrying out the method of the present invention, changes in APM propagation loss are measured, and these changes will be particularly noticeable during the time that a liquid will undergo phase transition and become a solid, or vice versa. To measure these changes, a signal of fixed frequency and amplitude is input to the device while changes in the output signal amplitude are monitored. Suitable means are used for generating the signal, such as a Hewlett-Packard 8656A synthesized source, which is capable of providing an RF signal at about 158 MHz. A Hewlett-Packard 8508A vector voltmeter has been employed successfully in order to monitor the signal level from the output transducer 20. The difference in the input and output signal levels is the measure of the insertion loss, which includes both transduction and propagation losses. Data from the various components of the present system are preferably recorded as a function of time by a computer such as a Hewlett-Packard 9816. The above-described apparatus makes it possible to consistently monitor the large changes in propagation loss which occur upon freezing so as to determine precisely when a phase transition event occurs. In this apparatus, the interpretation of the signal received corresponds to the attenuation of the high frequency mechanical wave generated in the apparatus which is then used to determine the physical state of the material undergoing the phase transition.

Figure 2:
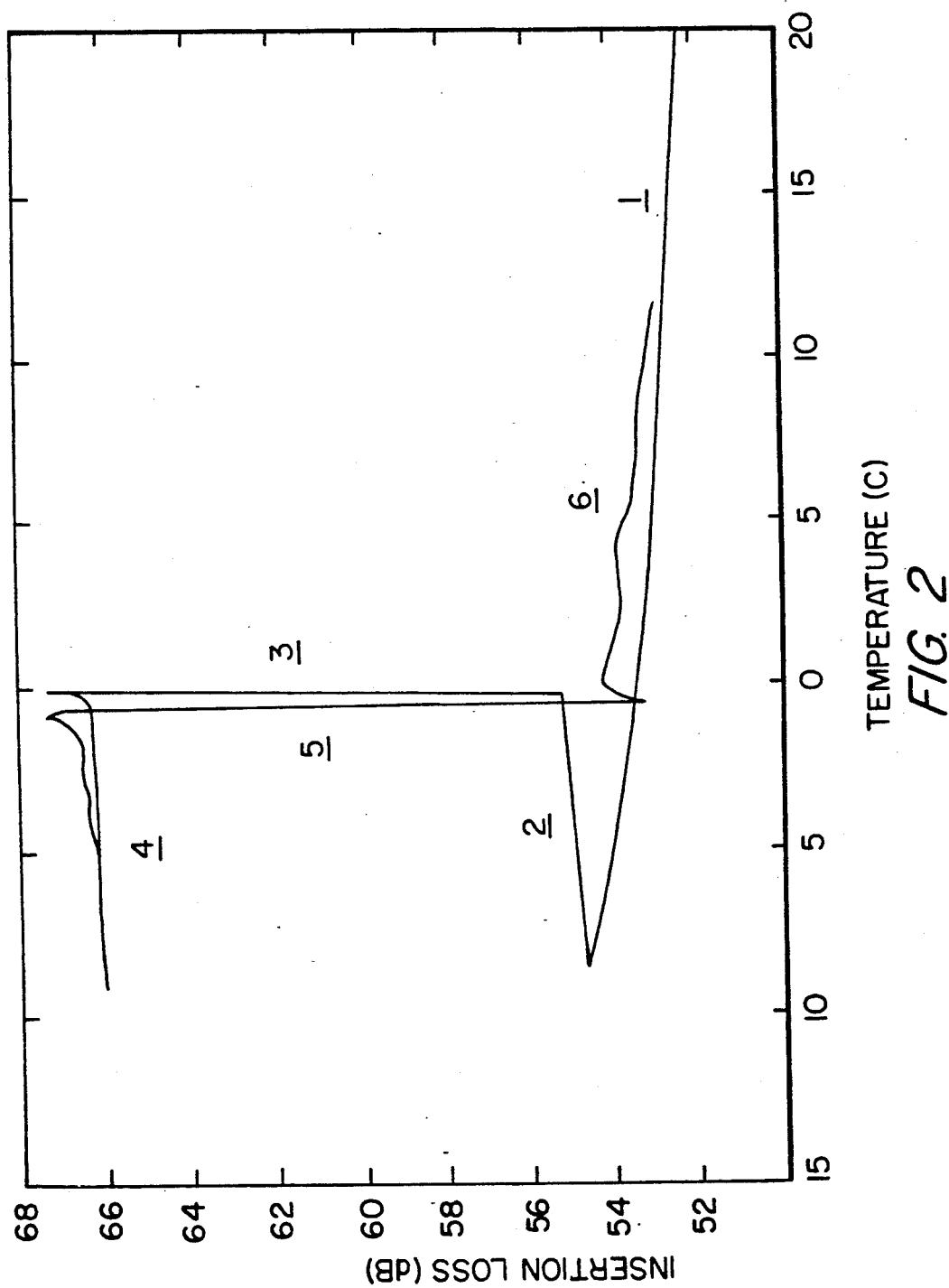
FIG. 2 is a graphic representation of the pattern of insertion loss recorded during the freezing of a liquid material detected by the device of the present invention.

The apparatus described above has been used successfully to monitor liquid-to-solid phase transition events in a manner that can be utilized in applications such as determining icing on airplane wings. In an operation according to the present invention, a sample of doubly distilled water of about one milliliter in volume was placed in the teflon cell of the invention, and the insertion loss was monitored. A graphic representation of the insertion loss over a range of temperatures for the distilled water can be observed in FIG. 2. In this graph, insertion loss is plotted as a function of water temperature which was taken from 20° C. down to −8° C., and then back up to 12° C. In this operation, the increase in insertion loss when water was initially added to the dry APM device surface at 25° C. amounted to about 5 dB over the 0.75 cm path length between input and output transducers. A sequence of events which occurred during the phase changes undergone by the distilled water are numbered on the graph and are indicated as follows:

(1) As the water cools, its viscosity increases and causes gradually higher viscous attenuation of the signal. The water supercools to about −8° C. before freezing begins;

(2) As nucleation of the first ice crystals occurs, the temperature of the water/ice mixture jumps immediately to 0° C. There is little increase in insertion loss at this point;

(3) The two-phase water/ice mixture continues to freeze at constant temperature (0° C.), and shows a steady increase in attenuation which accompanies the phase change;

(4) When all the water has turned to ice, the temperature of the ice decreases toward the temperature of the surrounding environmental chamber, −8° C.;

(5) The chamber temperature was then increased up to 20° C., causing the ice to melt. The ice/water mixture remained at 0° C. as melting proceeded with the APM device insertion loss retracing the path followed during freezing;

(6) When the ice had completely melted, the water temperature increased, and this resulted in a decrease in the viscous attenuation.

In further experiments, the APM sensor was used to measure the phase transition in a solution of distilled water and ethylene glycol, the major constituent of anti-freeze. In this case, the ethylene glycol was added after the ice was fully formed and had cooled to $-8°$ C. Again in these tests, the initial cooling of the water produced only a small increase in loss, but this loss increased as the two-phase system froze at 0° C. After the water had frozen, further ethylene glycol was added to the cell, and the melting event at the lower temperature of the mix was also successfully monitored by the APM device of the present invention.

To correlate the magnitude of viscous damping of the APM with liquid viscosity, a series of glycerol/water mixtures having range of viscosities between 1 and 62 cP were used. With liquid contacting the entire unelectroded side of the APM wave path, including the transducer regions, changes in loss $\Delta L$ (in db) due to changes in liquid shear viscosity $\Delta \eta$ (in Poise) are found to be given by the following equation:

$$\Delta L = 25\sqrt{\Delta \eta}$$

These experiments further indicated that with the liquid in contact with the APM device, the insertion loss is determined by the liquid viscosity. The increase in loss measured during cooling can be attributed to an increase in the shear viscosity of the fluid.

The results of tests performed with APM devices and the method of the present invention indicate that these devices are very sensitive to liquid-solid phase transitions, and thus can be useful in a method of detecting phase transition events such as icing on airplane wings. Liquid water contacting the device contributes about 5-7 db of loss, depending on the liquid temperature, while ice contacting the device contributes generally an additional 11-12.5 db of loss. The loss values thus provide unambiguous and reproducible information about whether a medium contacting the device surface is entirely liquid or entirely solid. The information thus received can be used to determine a phase transition event independent of the temperature of the surface where the material is tested. This is important because temperature measurement alone can be ambiguous as indicated in the cases wherein distilled water supercools so that it is still liquid even though the temperature is below 0° C. It is thus clear that liquid-solid phase transition events can be accurately detected using the high frequency mechanical waves generated by the device of the present invention.

The present invention can also be useful in detecting the binding of the material to a particular surface. This is possible due to the variation in loss which will differ between the state when a solid is in contact with the acoustic plate mode detecting element as to when the solid is no longer in contact with the detecting element. In general, because the signals generated by the acoustic wave device of the present invention which will be attenuated to the degree dependent on the physical state of the material in contact with the detecting element, the device can also be used to detect the degree of adhesion of a given material. When materials are more tightly bound to the detecting element, this attenuates the wave in a different manner than when a material is less tightly bound to the element.

Figure 3:
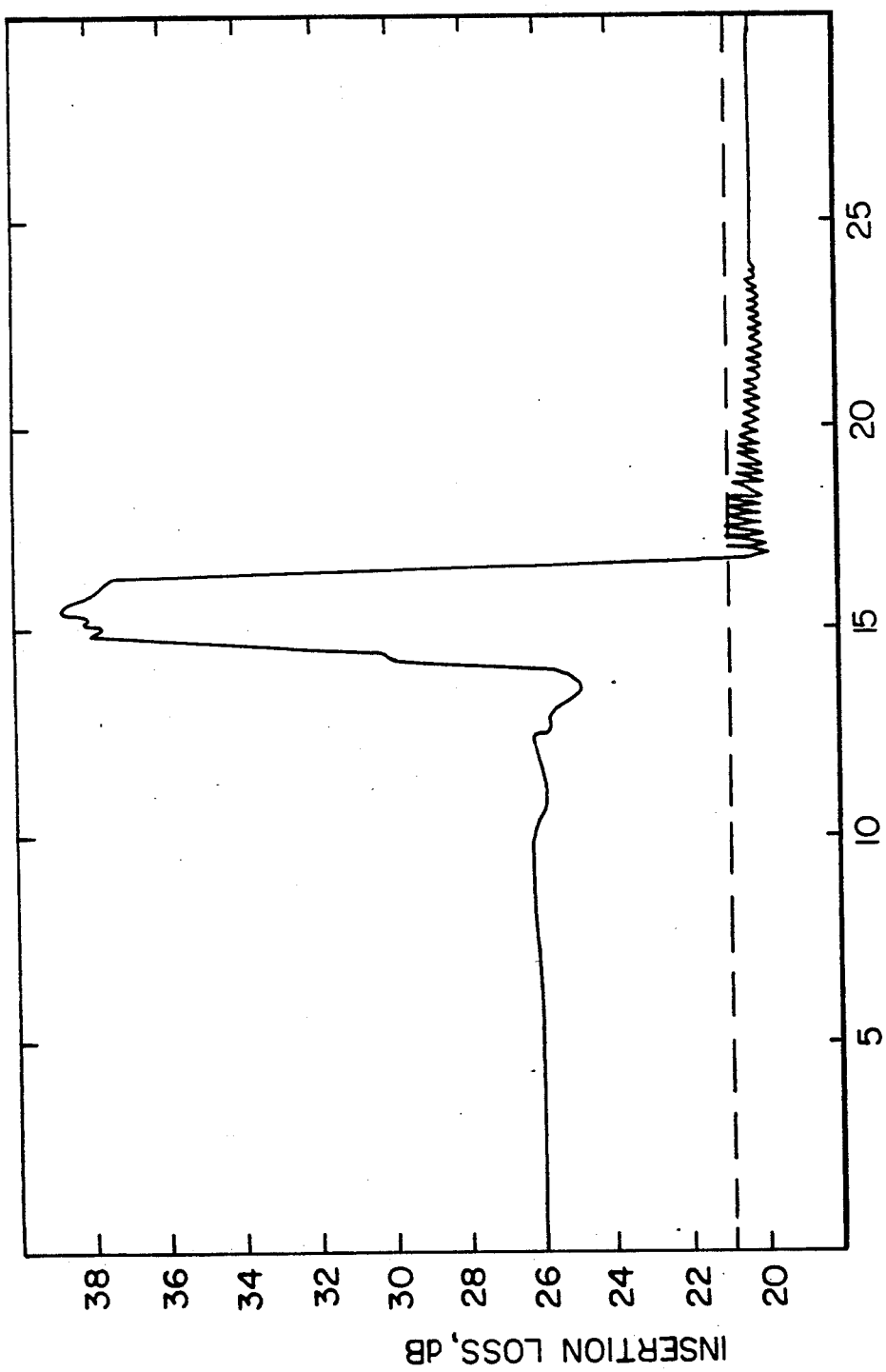
FIG. 3 is a graphic representation of the insertion loss measured during the monitoring of the freezing of gallium metal using the device of the present invention.

The ability of the device of the present invention to measure the solid/solid interface of material so that binding to a particular surface can be measured was investigated by monitoring the freezing of gallium metal. The graphic representation of the insertion loss was recorded while monitoring the freezing of gallium metal or liquid gallium melt using a cell in contact with the detecting element of the present invention, and this graph can be observed in FIG. 3. As observed in this figure, the variation in loss measured as the Ga solified on the APM sensor was indicative of the various phases of the material. In the graph, the dashed line indicates the loss obtained with a free or unperturbed device surface. When liquid gallium (melting point 29.8° C.) was placed on the device surface, this resulted in approximately 5 dB of viscous loss. Solidification of the contributed an additional 13 dB of loss. After about two minutes, however, the loss was observed to drop precipitously to near the free-surface value. The readings apparently corresponded to the delamination of the solid Ga from the quartz surface of the APM device. Following the experimental readings, a piece of Ga was found to be completely free on the quartz device surface. It has been found previously that simply placing a solid, such as a piece of glass or solid gallium on the APM device surface does not produce any measurable propagation loss.

It appears thus that while the viscosity of an adjacent liquid determines propagation loss, with an adjacent solid it is the elastic properties, such as density and stiffness parameters and solid dissipation parameters, which dictate loss. If the solid is sufficiently well-bound to the APM device, a non-slip boundary condition will exist at the solid/solid interface. In this case, shear motion of the device substrate will couple shear motion into the adjacent solid and this will lead to the radiation of acoustic energy into the latter which greatly increases propagation loss.

The test of solidification of Ga on the APM device surface provides further information regarding the effects of the nature of the solid/solid contact on propagation loss. In the experiment, the sudden decrease in loss was observed at a point where spontaneous delamination of the Ga from the quartz surface occurred. This would suggest that in this case, the bonding between the Ga and the quartz is transitory, i.e., that the solid initially bonds sufficiently well to insure a non-slip boundary, but then suddenly debonds and allows boundary slippage which no longer results in perturbations of the APM device. These experiments show that the APM can be useful in determining not only the liquid-to-solid phase transition events, but whether or not such phase change events result in the intimate bonding of a solid to the APM surface. It is possible that the surface of the piezoelectric substrate used in the present device may be coated with a thin film of any desired material to allow examination of adhesion between the substance undergoing a phase change and the thin film of material.

The present apparatus and method thus provide an improved means for detecting phase transition events such as from a liquid to a solid, and can also be useful in assessing the level of adhesion between a solid material and the surface of the device. It is contemplated that uses for the sensing device and method will include monitoring the icing of aircraft wings or other surfaces where the freezing of water and the sticking of ice can cause problems and evaluating the efficacy of chemical or biological agents designed to prevent frost damage to crops. The present apparatus and method will thus be particularly useful in applications that require the remote detection of a freezing or thawing event, particularly in cases where temperature alone will not be a reliable guide.

What is claimed is:

1. A method of detecting the adhesion of a solid material to a particular surface comprising:
   a) providing an acoustic plate mode detecting element capable of generating a high-frequency mechanical wave and positioning the element so that it can be contacted by a material to be detected with regard to degree of adhesion;
   b) contacting the acoustic plate mode detecting element with the material to be detected with regard to degree of adhesion;
   c) generating a high-frequency mechanical wave through said acoustic plate mode detecting element which is attenuated to a degree dependent on the adhesion of the material to be detected in contact with the detecting element;
   d) measuring the attenuation of said high frequency mechanical wave caused by the adhesion of the material with the detecting element;
   e) and using the measure of attenuation to determine the adhesion between the material to be detected and the detecting element.

2. A method according to claim 1 wherein a thin film of material is placed on the surface of the detecting element so that the adhesion measured is between the material to be detected and the thin film of material.

* * * * *